(12) United States Patent
Schweers et al.

(10) Patent No.: US 6,448,448 B1
(45) Date of Patent: Sep. 10, 2002

(54) PROCESS FOR THE NON-OXIDATIVE PREPARATION OF FORMALDEHYDE FROM METHANOL

(75) Inventors: Elke Schweers, Bad Soden; Rolf Schulz, Frankfurt; Thomas Kaiser, Kelkheim; Uwe Dingerdissen, Seeheim-Jugenheim, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/424,981

(22) PCT Filed: May 26, 1998

(86) PCT No.: PCT/EP98/03083

§ 371 (c)(1),
(2), (4) Date: Feb. 22, 2000

(87) PCT Pub. No.: WO98/55435

PCT Pub. Date: Dec. 10, 1998

(30) Foreign Application Priority Data

Mar. 31, 1998 (DE) .......................................... 198 14 284

(51) Int. Cl.$^7$ ......................... C07C 47/052; F28D 21/00
(52) U.S. Cl. ......................... 568/420; 568/426; 568/602; 422/198; 422/202; 422/203
(58) Field of Search ............................... 568/420, 426, 568/602; 549/368; 422/198, 202, 203

(56) References Cited

U.S. PATENT DOCUMENTS 4,010,208 A * 3/1977 Aicher et al. ................ 260/603
4,990,685 A * 2/1991 Alpers et al. ................ 568/491

* cited by examiner

Primary Examiner—Sreeni Padmanabhan
Assistant Examiner—Sikarl A. Witherspoon
(74) Attorney, Agent, or Firm—Connolly Bove Lodge & Hutz LLP

(57) ABSTRACT

The invention relates to a method for producing formaldehyde from methanol by non-oxidative dehydrogenation, in a reactor, in the presence of a catalyst at a temperature between 300 and 1000° C. Said method is characterized in that the generation of the catalyst takes place spatially separate from the reactor and at a temperature greater than the dehydrogenation.

7 Claims, 2 Drawing Sheets

PROCESS FOR THE NON-OXIDATIVE PREPARATION OF FORMALDEHYDE FROM METHANOL

This application is a 371 of PCT/EP98/09083, filed May 26, 1998, now Ser. No. 98/55435, published Dec. 10, 1998.

A number of processes for preparing formaldehyde from methanol are known (see, for example, Ullmann's Encyclopaedia of Industrial Chemistry). The processes carried out industrially are predominantly the oxidation $$CH_3OH + \tfrac{1}{2}O_2 \rightarrow CH_2O + H_2O$$

over catalysts comprising iron oxide and molybdenum oxide at from 300° C. to 450° C. (Formox process) and the oxidative dehydrogenation (silver catalyst process) according to:

$$CH_3OH \rightarrow CH_2O + H_2H_2 + \tfrac{1}{2}O_2 \rightarrow H_2O$$

at from 600° C. to 720° C. In both processes, the formaldehyde is first obtained as an aqueous solution. Particularly when used for the preparation of formaldehyde polymers and oligomers, the resulting formaldehyde has to be subjected to costly dewatering. A further disadvantage is the formation of corrosive formic acid, which has an adverse effect on the polymerization, as by-product.

The dehydrogenation of methanol enables these disadvantages to be avoided and enables, in contrast to the abovementioned processes, virtually water-free formaldehyde to be obtained directly:

$$CH_3OH \xrightarrow{cat.} CH_2O + H_2$$

In order to achieve an ecologically and economically interesting industrial process for the dehydrogenation of methanol, the following prerequisites have to be met: The strongly endothermic reaction has to be carried out at high temperatures so as to be able to achieve high conversions. Competing secondary reactions have to be suppressed in order to achieve satisfactory selectivity to formaldehyde (without catalysis, the selectivity for the formation of formaldehyde is less than 10% at conversions over 90%). Residence times have to be short and the cooling of the reaction products has to be rapid in order to lessen the decomposition of the formaldehyde which is not thermodynamically stable under the reaction conditions:

$$CH_2O \rightarrow CO + H_2$$

Various methods of carrying out this reaction have been proposed; thus, for example, DE-A-37 19 055 describes a process for preparing formaldehyde from methanol by dehydrogenation in the presence of a catalyst at elevated temperature. The reaction is carried out in the presence of a catalyst comprising at least one sodium compound at a temperature of from 300° C. to 800° C.

J. Sauer and G. Emig (Chem. Eng. Technol. 1995, 18, 284–291) were able to set free a catalytically active species, which they presume to be sodium, from a catalyst comprising $NaAlO_2$ and $LiAlO_2$ by means of a reducing gas mixture (87% $N_2$ + 13% $H_2$). This species was able to catalyze the dehydrogenation of methanol introduced at a downstream point in the same reactor, i.e. not coming into contact with the catalyst bed, to give formaldehyde. When using non-reducing gases, only a low catalyst activity was found.

According to J. Sauer and G. Emig and also results from more recent studies (see, for example, M. Bender et al., paper presented to the 30th annual meeting of German catalyst technologists, March 21–23, 1997), sodium atoms and NaO molecules were identified as species emitted into the gas phase and their catalytic activity for the dehydrogenation of methanol in the gas phase was described.

In the known processes, the starting material methanol is always diluted with nitrogen and/or nitrogen/hydrogen mixtures for the reaction.

Although good results are achieved with the known processes, there is nevertheless considerable room for improvement from a technical and economic point of view, particularly because the catalysts employed become exhausted or inactivated over time and the formaldehyde yields are still capable of improvement.

It has surprisingly been found that it is possible to increase the yield in the dehydrogenation of methanol by means of an improved reaction procedure. This can be achieved by setting separate temperatures and possibly also residence times in the primary catalyst decomposition zone and the reaction section, particularly when the temperature level in the actual reaction section is set at a lower value than in the primary catalyst addition unit.

In this way, methanol conversions of more than 95% and high formaldehyde selectivities can be achieved and, surprisingly, non-reducing gases can also be used as carrier gas.

The invention accordingly provides a process for preparing formaldehyde from methanol by dehydrogenation in a reactor in the presence of a catalyst at a temperature in the range from 300 to 1000° C., wherein the catalyst is generated spatially separately from the reactor and at a temperature above the dehydrogenation temperature.

Advantages of a lower reaction temperature are the lower energy and apparatus requirements for heating/cooling before/after the reaction, the low decomposition rate of the formaldehyde which is thermally unstable under the reaction conditions and the lower demands placed on the materials of construction.

The temperature difference is preferably at least 20° C., particularly preferably from 40 to 250° C.

When suitable primary catalysts are thermally treated in the primary catalyst decomposition zone and a reducing or even non-reducing gas such as molecular nitrogen is passed over them at a temperature which is not the same as the reaction temperature for the dehydrogenation, but is higher, one or more catalytically active species are released or generated and/or generated on them (secondary catalyst) and these species are able to catalyze the dehydrogenation of methanol. Such a fluid catalyst can be transported over considerable distances without suffering an appreciable loss of effectiveness in the dehydrogenation. This separate setting of the temperature allows, by matching to the respective conditions for catalyst liberation/vaporization or generation of a catalytically active species (secondary catalyst) on the one hand and for the reaction on the other hand, the possibility of, in particular, lowering the reaction temperature. This reduces the decomposition of the unstable formaldehyde as a result of subsequent reactions and increases the yield.

Preferred temperatures for generating the catalytically active species from the primary catalyst are from 300 to 1100° C.; particular preference is given to temperatures of from 400 to 1000° C.

Preferred temperatures for the dehydrogenation of the methanol are from 200 to 1000° C.; particular preference is given to temperatures of from 300 to 980° C.

Furthermore, the residence times in the dehydrogenation reactor and the vessel for primary catalyst addition or for generating the secondary catalyst can be set separately by dividing the carrier gas stream. A specific loading of the gas stream passed through the catalyst addition unit with the active species is achieved in this way.

Preferred residence times for generating the secondary catalyst are from 0.01 to 60 sec, particularly preferably from 0.05 to 3 sec, very particularly preferably from 0.05 to 1 sec. To dehydrogenate the methanol, preference is given to residence times in the reaction zone of from 0.005 to 30 sec, particularly preferably from 0.01 to 15 sec, very particularly preferably from 0.05 to 3 sec.

Replacement of the exhausted primary catalyst makes possible a continuous process for the non-oxidative dehydrogenation of methanol which gives improved methanol utilization or formaldehyde yields.

The carrier gas streams can consist of a reducing or a non-reducing gas, e.g. $H_2/CO$ mixtures or nitrogen, preferably the by-products of the dehydrogenation.

Figure 1:
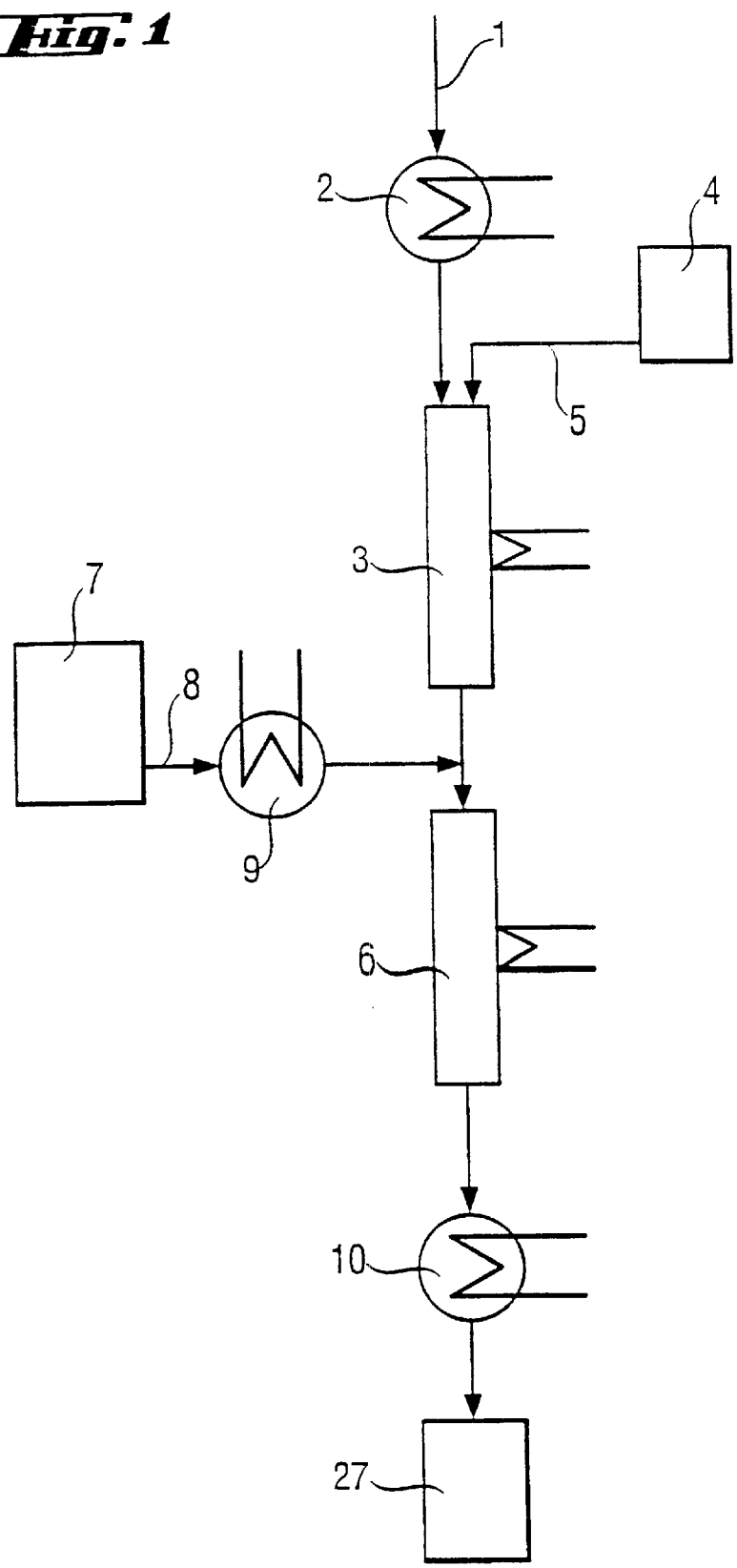
FIG. 1 shows a schematic overview of a preferred variant of the process of the invention.

The carrier gas stream 1 is heated in the heat exchanger 2 and introduced into one or more heated vessels 3 in which the active catalyst species is generated. From a reservoir 4, primary catalyst 5 is likewise fed into the vessel 3. The stream leaving vessel 3 is introduced into the reactor 6. Methanol 8 is conveyed from a reservoir 7, heated in a heat exchanger 9 and fed to the reactor 6. The product gases from the reactor 6 are cooled in the heat exchanger 10 and fed to a unit 27 for separating off the formaldehyde.

The invention thus also provides an apparatus for carrying out the abovementioned process comprising one or more heat exchangers for preheating the starting materials, a heated vessel for decomposing the primary catalyst, a heated reactor for carrying out the dehydrogenation, one or more heat exchangers for cooling the product mixture, a unit for separating off the formaldehyde, an apparatus for introducing the methanol and for feeding in further primary catalyst and also means of setting different temperatures in the vessel for decomposing the primary catalyst and in the reactor.

Further primary catalyst can be introduced as a solid, as a solution in a liquid solvent or as a melt, in each case continuously or discontinuously.

An advantage of the continuous or discontinuous metering in or further introduction of the primary catalyst is a plant operating time which is independent of the catalyst starting material originally added and is significantly lengthened. Further advantages of the separate addition are a targeted and defined introduction of the active substance and the opportunity of uniform provision of the catalytically active species.

The further introduction of the primary catalyst as a solid, e.g. pulverulent, granular or compacted, is carried out by means of solids metering, e.g. using a reciprocating or rotary piston, a cellular wheel feeder, a screw or a vibrating chute.

If the primary catalyst, e.g. sodium or a sodium compound, is added in solution form, particularly suitable solvents are those having a chemical composition consisting of only the elements already present in the process (C, H, O). Particular preference is given to MeOH as solvent. The solution is added, for example, via a nozzle which can be cooled in order to avoid vaporization of the solvent or crystallization or deposition of the solid primary catalyst in the nozzle.

The primary catalyst can be added as a melt, for example, via a nozzle. The melt can then be vaporized or decomposed directly in the gas stream.

For all possible ways of introducing further primary catalyst, this is advantageously carried out in such a way that the material is in intimate contact with flowing gas. This can be achieved, for example, by applying the catalyst material by the above-described methods onto a suitable surface over which the gas flows. This can be the surface of a support material present in a fixed bed. Suitable materials are, for example, SiC, $SiO_2$, $Al_2O_3$, etc. in an appropriate geometric form, e.g. as granules, pellets or spheres. The support material is preferably arranged vertically in a fixed bed, preferably with metering-in from above. The substance which is introduced deposits on the support material and the catalytically active substance goes into the gas phase during the process.

Another possibility is placing the primary catalyst in a fluidized bed through which the carrier gas stream is passed. Here, the fluidized material consists at least partly of the supported or unsupported primary catalyst. The loss of active substance can be made up by introducing further fresh primary catalyst; exhausted material can, if desired, be taken off. This can be realized in the continuous case, for example, by means of a circulating fluidized bed.

The further introduction of a primary catalyst can also be carried out by alternating secondary catalyst generation in different vessels in which the primary catalyst can be located, for example, as a fixed bed or a fluidized bed, in each case supported or unsupported.

The advantage of using a plurality of units for the discontinuous introduction of further catalyst is that it is also possible to use primary catalysts for which, e.g. owing to material properties such as melting point, viscosity or decomposition temperature, continuous feeding would be impossible or possible only with great difficulty.

Compounds which can be used in the process of the invention are, for example, catalysts known from the literature, as are described, for example, in Chem. Eng. Technol. 1994, 17, 34.

Suitable metals are, for example, Li, Na, K, Cs, Mg, Al, In, Ga, Ag, Cu, Zn, Fe, Ni, Co, Mo, Ti, Pt, or their compounds. Also suitable are, for example, S, Se, phosphates of transition metals such as V and Fe, and heteropolyacids such as molybdophosphoric acid.

Examples of specific catalysts are:

Sodium or sodium compounds (DE-A-37 19 055 and DE-A-38 11 509)

Aluminum oxide, alkali metal aluminate and/or alkaline earth metal aluminate (EP-A-04 05 348)

Silver oxide (JP-A 60/089 441, Derwent Report 85-15 68 91/26)

A catalyst comprising copper, zinc and sulfur (DE-A 25 25 174)

A catalyst comprising copper, zinc and selenium (U.S. Pat. No. 4,054,609)

A catalyst comprising zinc and/or indium (EP-A 0 130 068)

Silver (U.S. Pat. No. 2,953,602)

Silver, copper and silicon (U.S. Pat. No. 2,939,883).

Compounds containing zinc, cadmium, selenium, tellurium or indium.

Preference is given to using sodium or sodium compounds.

The form in which such a catalyst, for example a sodium-containing catalyst, is used can vary widely:

Metallic, e.g. also as an alloy with at least one other alloy constituent, as compound or salt, where at least one nonmetallic element is chemically combined with Na (binary compounds and salts). If more than one element is present in chemically combined form in the compound, a binary, ternary or quarternary compound or a salt is present. Use of the catalyst in supported form, for example on an inorganic support, is likewise preferred.

If sodium is used in metallic form, it can be used as solid, liquid or preferably as vapor.

Preferred alloys are those with other alkali metals and/or alkaline earth metals, for example Ba, Sr, Ca, Cs, Rb, K or, particularly preferably, Li and/or magnesium.

Furthermore, alloys with B, Al, Si and Sn can also be used. This also applies, in particular, to alloys which can comprise compounds such as sodium boride, $NaB_2$, sodium silicide, NaSi or NaSn.

Examples of suitable binary sodium compounds and salts are sodium carbides such as $Na_2C_2$, $NaC_8$, sodium halides such as NaF, sodium oxides such as $Na_2O$, sodium azide, sodium phosphide, sodium sulfide, sodium polysulfides, preferably also sodium hydrides such as NaH.

Examples of suitable ternary sodium compounds and salts are sodium borates such as borax, sodium phosphates or hydrogenphosphates, sodium phosphites, sodium (meta) silicates and aluminosilicates, e.g. water glass, $Na_3AlF_6$ (cryolite), sodium (hydrogen)sulfate, sodium sulfite, sodium nitrite, sodium nitrate, sodium amide, sodium acetylide NaCCH, sodium cyanide, sodium thiocyanate, the sodium salt of methyl thiol, sodium thiosulfate, but preferably NaOR, where R=H or an organic radical (=salts of organic acids, alkoxides, phenoxides, acetylacetonate, acetoacetic ester salt, salts of salicylic acid or salicylaldehyde), sodium carbonate and sodium hydrogencarbonate and mixtures thereof, for example soda, thermonatrite, trona, pirssonite, natrocalcite. The use of anhydrous, i.e. dried, salts is generally preferred. Particular preference is given to NaOH, NaOOC-R' (preferably formate, acetate, lactate, oxalate), NaOR' (R' is an organic radical having from 1 to 4 carbon atoms) and sodium carbides. Very particular preference is given to NaOH, sodium formate, sodium methoxide, sodium acetate and sodium carbides such as $Na_2C_2$.

Suitable quaternary compounds are, for example, sodium-containing aluminosilicates which can be prepared synthetically or can also occur in a wide variety as natural minerals and rocks (e.g. sodium feldspar or albite and calcium-sodium feldspar or oligoclase). They can additionally be laden with Na by ion exchange.

Use can also advantageously be made of double salts of the alun type or thenardite, glauberite, astrakanite, glaserite, vanthoffite.

The sodium compounds and salts mentioned here can advantageously also be in the form of mixtures. In particular, it is also quite possible to use mixtures containing <50%, preferably <30%, of cations of other alkali metals and/or alkaline earth metals, e.g. Ba, Sr, Ca, Cs, Rb, K or preferably Li and/or magnesium. Industrially available, complex mixtures such as soda lime, ground basic slag and cements, e.g. Portland cement, if desired after enrichment with sodium by storage in sodium-containing solutions (NaCl, sea water) are particularly advantageous.

To prepare the fluid catalyst, the compounds which are thermally treated are particularly advantageously compounds which, apart from sodium, contain only the elements C, 0 and H which are already present in the process so that they are consumed in the process without leaving a significant residue. It is particularly advantageous that technical-grade compounds can thus also be used as catalyst.

Preference is generally given to the use of water-free, i.e. dried, compounds.

Particularly preferred primary catalysts are sodium compounds selected from the group consisting of:
a) sodium alkoholates,
b) sodium carboxylates,
c) sodium salts of C-H acid compounds and
d) sodium oxide, sodium hydroxide, sodium nitrite, sodium acetylide, sodium carbide, sodium hydride and sodium carbonyl.

In the process of the present invention, the abovementioned compounds give formaldehyde yields of over 60% and low water concentrations of less than 5 mol % of $H_2O$ per mole of formaldehyde at reaction temperatures of from 600 to 1000° C.

Suitable reactors are well known to those skilled in the art. Essentially, it is possible to use reactor types and assemblies as are known from the literature for dehydrogenation reactions, with the corrosive properties of substances which may be present in the fluid stream having to be taken into account. Such apparatuses are described, for example, in Winnacker/Küchler, Chemische Technologie, 4th Edition, chapter "Technik der Pyrolyse" ["Pyrolysis Technology"], Hanser Verlag, Munich 1981–86.

Suitable reactor materials are, for example, ceramic materials such as α-alumina, but also iron- and nickel-based alloys which are resistant to carbonization, heat and scale, e.g. Inconel600® and Hasteloy®. If combustion is used for heating the vessel 3 and/or the reactor 6, externally fired tubes, for example, are suitable for this purpose.

The heat to be supplied to the process is preferably obtained by the combustion of by-products of the dehydrogenation, especially $H_2$ and CO.

The heating of the reactor/catalyst vessel by means of microwaves is likewise preferred.

The reaction can be carried out using commercial methanol; it should preferably be low in water and should contain no substances which poison the catalyst.

To carry out the dehydrogenation, the fluid, preferably gaseous, methanol is preferably diluted with carrier gas.

The molar proportion of methanol is generally from 5 to 90%, preferably from 10 to 50%, particularly preferably from 10 to 40%.

The pressure in the process of the invention is not critical. The dehydrogenation of the methanol can be carried out at subatmospheric pressure, atmospheric pressure or superatmospheric pressure. A range from about 0.1 to 10 bar, preferably from 0.5 to 2 bar, is particularly suitable. Preference is given to atmospheric pressure. The process of the invention can be carried out discontinuously or continuously, with the latter being preferred.

In a preferred variant of the process of the invention, a further carrier gas stream which is at a temperature above, preferably at least 20° C. above, particularly preferably from 40 to 250° C. above, the dehydrogenation temperature is introduced.

In a preferred variant of the process of the invention, a circulating gas stream comprising by-products of the dehydrogenation is passed as carrier gas through the reactors. This circulating gas stream is obtained by, after separating off the formaldehyde, recirculating at least some of the by-products of the dehydrogenation, especially $H_2$ and CO, to the reactor by means of a suitable apparatus.

The formaldehyde can be separated from the reaction mixture by methods known per se with which those skilled in the art are familiar, for example by polymerization, condensation or physical or chemical absorption or adsorption.

An industrially proven method is the formation of hemiacetals from formaldehyde and an alcohol, The hemiacetals are subsequently dissociated thermally, giving very pure formaldehyde vapor. The alcohol used is usually cyclohexanol since its boiling point is sufficiently far above the decomposition temperature of the hemiacetal. The hemiacetals are usually dissociated in falling film or thin film evaporators at temperatures of from 100 to 160° C. (see, for example, U.S. Pat. No. 2,848,500 of Aug. 19, 1958 "Preparation of Purified Formaldehyde" and U.S. Pat. No. 2,943,701 of Jul. 5,1960 "Process for purification of gaseous formaldehyde", or JP-A 62/289 540). The formaldehyde vapors liberated in this dissociation still contain small amounts of impurities which are usually removed by countercurrent scrubbing with an alcohol such as cyclohexanol hemiformal, by condensation or by controlled prepolymerization.

Particularly preferred methods for purifying the formaldehyde prepared according to the invention are described in the German patent applications 19 747 647.3 and 19 748 380.1.

A further method of separating formaldehyde from the reaction mixture is the formation of trioxane in a catalytic gas-phase process (see, for example, Appl. Catalysis A 1997, 150, 143–151 and EP-A 0 691 338). Trioxane can then, for example, be condensed out.

Possible ways of utilizing the by-products of the reaction, in particular hydrogen, are, for example, the synthesis of methanol or the isolation of pure hydrogen which can be, for example, separated off by means of membranes.

Hydrogen obtained in this way is suitable, for example, for the synthesis of ammonia, in refinery processes for producing gasoline and petrochemical cracking products, for the synthesis of methanol, for hardening fats and for other hydrogenations, as reducing agent for producing W, Mo, Co and other metals, as reducing protective gas in metallurgical processes, for autogenous welding and cutting, as fuel gas in admixture with other gases (town gas, water gas), or in liquefied form as fuel in aerospace applications.

The formaldehyde prepared by the process of the invention is suitable for all known fields of application, for example corrosion protection, production of mirrors, electrochemical coatings, for disinfection and as a preservative, likewise as intermediate for preparing methanolic formaldehyde solutions, methylal, plastics, for example polyoxymethylenes, polyacetals, phenolic resins, melamines, aminoplastics, polyurethanes and casein plastics, and also 1,4-butanol, trimethylolpropane, neopentyl glycol, pentaerythritol and trioxane, for producing dyes such as fuchsin, acridine, for producing fertilizers and for treating seed.

Since formaldehyde prepared by the process of the invention usually has a low water content, formaldehyde prepared in this way is particularly suitable for polymerization to form polyoxymethylene and trioxane, since anhydrous formaldehyde has to be used in this polymerization.

The invention also relates to plastics such as polyoxymethylene and polyacetals, trioxane, dyes, fertilizers and seed produced in such a way.

The invention further provides a process for preparing trioxane, which comprises 1. converting methanol into formaldehyde by dehydrogenation in a reactor at a temperature in the range from 300 to 1000° C. in the presence of a catalyst, where the catalyst is generated physically separately from the reactor and at a temperature above the dehydrogenation temperature, and 2. if desired, purifying the formaldehyde prepared in this way and trimerizing to give trioxane.

Details of the preparation of trioxane are well known to those skilled in the art. They are described, for example, in Kirk-Othmer, Encyclopedia of Chemical Technology, 2nd edition, volume 10, pp. 83, 89, New York Interscience 1963–1972.

The invention likewise provides a process for preparing polyoxymethylene, which comprises 1. converting methanol into formaldehyde by dehydrogenation in a reactor at a temperature in the range from 300 to 1000° C. in the presence of a catalyst, where the catalyst is generated physically separately from the reactor and at a temperature above the dehydrogenation temperature, and 2. if desired, purifying the formaldehyde obtained in this way, 3. polymerizing the formaldehyde, 4. capping the end groups of the polymer prepared in this way and 5. if desired, homogenizing the polymer in the melt and/or providing it with suitable additives.

The preparation of polyoxymethylene from formaldehyde is well known to those skilled in the art. Details may be found, for example, in Ullmann's Encyclopedia of Industrial Chemistry, volume 21, 5th edition, Weinheim 1992, and the literature cited therein.

The invention further provides a process for preparing polyoxymethylene copolymers, which comprises 1. converting methanol into formaldehyde by dehydrogenation in a reactor at a temperature in the range from 300 to 1000° C. in the presence of a catalyst, where the catalyst is generated physically separately from the reactor and at a temperature above the dehydrogenation temperature, and 2. trimerizing the formaldehyde obtained in this way to give trioxane, 3. if desired, purifying the trioxane, 4. copolymerizing the trioxane with cyclic ethers or cyclic acetals, 5. if desired, removing unstable e n d groups and 6. if desired, homogenizing the copolymer prepared in th is way in the melt and/or admixing is with suitable additives.

The invention further provides a process for preparing polyoxymethylene copolymers, which comprises 1. converting methanol into formaldehyde by dehydrogenation in a reactor in the presence of a catalyst at a temperature in the range from 300 to 1000° C., where a circulating gas stream comprising by-products of the dehydrogenation is passed through the reactor, and 2. if desired, purifying the formaldehyde obtained in this way, 3. copolymerizing the formaldehyde with cyclic ethers or cyclic acetals, 4. if desired, removing unstable end groups and 5. if desired, homogenizing the polymer prepared in this way in the melt and/or admixing it with suitable additives.

The preparation of polyoxymethylene copolymers is well known to those skilled in the art. Details may be found, for example, in Ullmann's Encyclopedia of Industrial Chemistry, volume 21, 5th edition, Weinheim 1992 and the literature cited therein and also in the Russian documents SU 436067, 740715 and SU 1755156, 720303.

The contents of the priority-establishing German patent applications 197 22 774.0 and 197 27 519.2 and also the abstract of the present application are expressly incorporated by reference into the present description.

Figure 2:
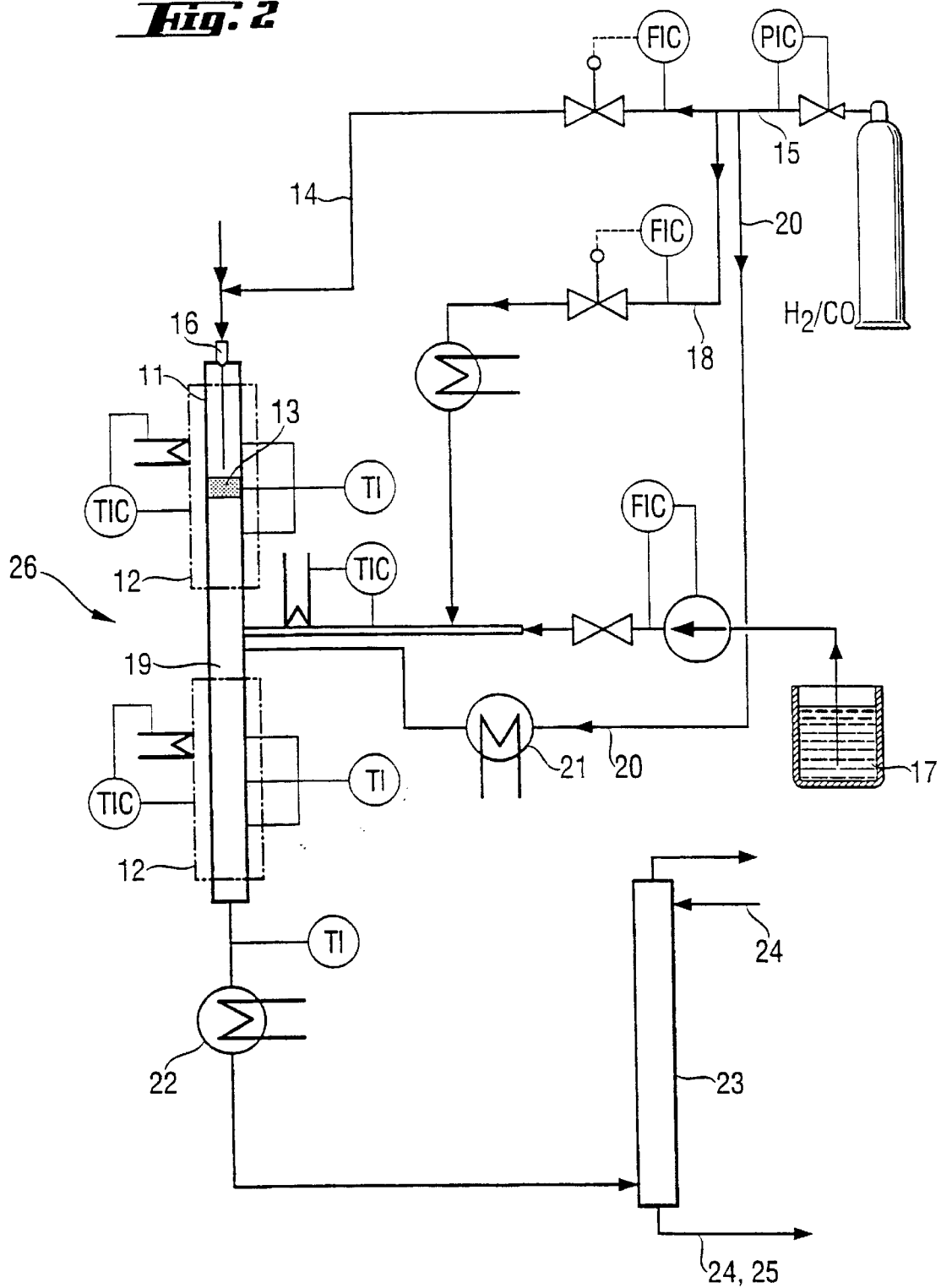

The invention is illustrated by the examples, without being restricted thereby. FIG. 2 schematically shows the configuration of the experimental apparatus by means of a process flow diagram.

EXAMPLES

The dehydrogenation of methanol is carried out in a tube reactor 26 which is heated indirectly by means of an electric tube furnace 12. A catalyst addition unit is made up of a metal tube 11 which is heated indirectly by means of the electric tube furnace 12 The tube 11 contains a bed 13 of support material on which the primary catalyst (0.1–5.0 g) is located. Part 14 of a superheated carrier gas stream 15 which has previously been preheated by means of heated feed lines is passed into this tube 11. In addition, further primary catalyst is introduced as a solution into this tube 11, via a nozzle 16. The primary catalyst is deposited on the bed 13.

The carrier gas substream 14 is passed through the bed in order to become laden with an active catalyst species which forms. The total stream is subsequently introduced into the reaction space 19.

Methanol 17 is preheated and fed into a further part 18 of the carrier gas stream 15 and is likewise introduced into the reaction space 19.

A third gas stream 20 which consists of pure carrier gas 15 is superheated 21, i.e. brought to a temperature which is above the dehydrogenation temperature, and likewise introduced into the reaction space 19.

The reaction space 19 is made up of a tube having length of 200–450 mm, internal diameter 4–21 mm. After leaving the reaction space 19, the product gases are quickly cooled to a temperature of less than 200° C. in a cooler 22 and are analyzed by means of a gas chromatograph. In a column 23, the reaction products are scrubbed with alcohol 24 (e.g. cyclohexanol at 20–80° C.) in order to separate off the formaldehyde 25. The primary catalyst used is sodium methoxide, the carrier gas used is $H_2$/CO or nitrogen. The total flow is 20–500 l/h. The methanol feed rate is such that a methanol concentration of about 5–20 mol % is established.

The formaldehyde yields given below are calculated as follows:

$$\text{Yield (in \%)} = \frac{\text{Formaldehyde formed (mol)}}{\text{Methanol fed in (mol)}} \cdot 100$$

A. Effect of temperatures

|  | Example 1 | Comparative example 1 | Comparative example 2 | Comparative example 3 | Example |
|---|---|---|---|---|---|
| Furnace temperature, catalyst decomposition | 900° C. | 900° C. | 750° C. | 750° C. | 950° C. |
| Furnace temperature, reactor | 750° C. | 900° C. | 750° C. | 900° C. | 800° C. |
| Yield of formaldehyde | 72% | 13% | 0.7% | 34% | 78% |

B. Effect of the residence time (residence times dependent)

(Residence times under normal conditions)

|  | Example 1 | Example 2 |
|---|---|---|
| Residence time in catalyst decomposition | 0.6 s | 1.2 s |
| Residence time in the reactor | 1.1 s | 2.2 s |
| Yield of formaldehyde | 72% | 67% |

C. Effect of the residence time (residence times independent)

(Residence times under normal conditions)

| Series 1 | Example 1 | Example 2 | Example 3 |
|---|---|---|---|
| Residence time in catalyst decomposition | 0.6 s | 1.2 s | 0.6 s |
| Residence time in the reactor | 1.1 s | 1.1 s | 0.55 s |
| Yield of formaldehyde | 72% | 77% | 63% |

(Residence time under normal conditions)

| Series 2 | Example 4 | Example 5 |
|---|---|---|
| Residence time in catalyst decomposition | 0.4 | 0.4 |
| Residence time in the reactor | 0.7 | 0.4 |
| Yield of formaldehyde | 68% | 78% |

What is claimed is:

1. A process for preparing formaldehyde from methanol by non-oxidative dehydrogenation in a reactor in the presence of a catalytically active species at a temperature in the range from 300 to 1000° C., wherein the catalytically active species is generated and/or released from a primary catalyst spatially separate from the reactor and at a temperature above the dehydrogenation temperature.

2. The process as claimed in claim 1, wherein the temperature difference between the catalyst generation and the dehydrogenation temperature is at least 20° C.

3. The process as claimed in claim 1, wherein a carrier gas stream having a temperature which is not the same as the dehydrogenation temperature is fed to the reactor.

4. The process as claimed in claim 1, wherein the primary catalyst used for generating the catalytically active species is continuously fed into the reactor.

5. The process as claimed in claim 3, wherein the carrier gas consists essentially of the by-products of the dehydrogenation.

6. The process as claimed in claim 1, wherein part of the by-product of the dehydrogenation is used as fuel for heating the reactor.

7. An apparatus for carrying out a process as claimed in claim 1 comprising one or more heat exchangers for preheating the starting materials, a heated vessel for decomposing, one ore more heat exchangers for cooling the product mixture, a unit for separating off the formaldehyde, an apparatus for introducing the methanol and for feeding in further primary catalyst and also means of setting different temperatures in the vessel for decomposing the primary catalyst and in the reactor.

* * * * *